US012551630B2

(12) United States Patent
Huang et al.

(10) Patent No.: US 12,551,630 B2
(45) Date of Patent: Feb. 17, 2026

(54) CONNECTOR FOR CONNECTING A MEDICAL INJECTION DEVICE TO A CONTAINER AND ASSEMBLY COMPRISING SAID CONNECTOR AND MEDICAL INJECTION DEVICE

(71) Applicant: Becton Dickinson France, Le Pont de Claix (FR)

(72) Inventors: Longxiang Huang, Suzhou (CN); Wilson Huang, Suzhou (CN)

(73) Assignee: Becton Dickinson France, Le Pont-de-Claix (FR)

( * ) Notice: Subject to any disclaimer, the term of this patent is extended or adjusted under 35 U.S.C. 154(b) by 903 days.

(21) Appl. No.: 17/767,215

(22) PCT Filed: Oct. 7, 2020

(86) PCT No.: PCT/EP2020/078024
§ 371 (c)(1),
(2) Date: Apr. 7, 2022

(87) PCT Pub. No.: WO2021/069455
PCT Pub. Date: Apr. 15, 2021

(65) Prior Publication Data

US 2022/0362482 A1 Nov. 17, 2022

(30) Foreign Application Priority Data

Oct. 8, 2019 (EP) .................................... 19306315

(51) Int. Cl.

| | |
|---|---|
| ***A61M 5/315*** | (2006.01) |
| ***A61J 1/20*** | (2006.01) |
| ***A61M 5/32*** | (2006.01) |

(52) U.S. Cl.
CPC ........ *A61M 5/31583* (2013.01); *A61J 1/2055* (2015.05); *A61J 1/2096* (2013.01); *A61M 5/3202* (2013.01)

(58) Field of Classification Search
CPC ........ A61M 5/1782; A61J 1/20; A61J 1/2065; A61J 1/2096
See application file for complete search history.

(56) References Cited

U.S. PATENT DOCUMENTS 2,864,364 A * 12/1958 Mizzy .................. A61M 5/283 604/203
5,454,409 A 10/1995 McAffer et al.
(Continued)

FOREIGN PATENT DOCUMENTS

CN 106691849 A * 5/2017
EP 0499481 B1 12/1996
(Continued)

OTHER PUBLICATIONS

Wang, CN 106691849 A machine translation (Year: 2017).*

*Primary Examiner* — Laura A Bouchelle
(74) *Attorney, Agent, or Firm* — The Webb Law Firm

(57) ABSTRACT

A connector for connecting a medical injection device having a distal tip, a needle extending from the distal tip and a sleeve extending around the tip comprising an inner threaded portion, to a container including a collar closed by a pierceable septum, including: a proximal part configured to sealingly engage the tip of the injection device so as to enclose at least a part of the needle; a distal part configured to be connected to the container, including a skirt configured to extend around the needle when the connector is connected to the injection device; and a needle shield configured to be mounted on the needle, so as to sealingly enclose at least the tip of the needle, the needle shield being configured to be
(Continued)

pierced by the needle inserted via the opening for sealingly enclosing said needle.

14 Claims, 7 Drawing Sheets

(56) References Cited

U.S. PATENT DOCUMENTS

| | | | | |
|---|---|---|---|---|
| 6,901,975 | B2 | 6/2005 | Aramata et al. | |
| 8,235,951 | B2 * | 8/2012 | Hund .................. | A61M 5/3202 604/199 |
| 9,919,826 | B2 * | 3/2018 | Ivosevic ............. | A61M 5/1626 |
| 10,814,069 | B2 | 10/2020 | Takemoto | |
| 2004/0097882 | A1 | 5/2004 | DiBiasi et al. | |
| 2007/0060904 | A1 | 3/2007 | Vedrine et al. | |
| 2015/0190586 | A1 | 7/2015 | Takemoto | |
| 2015/0265499 | A1 | 9/2015 | Takeuchi | |
| 2017/0065486 | A1 * | 3/2017 | Mosler .................. | A61J 1/2055 |
| 2018/0193228 | A1 | 7/2018 | David et al. | |

FOREIGN PATENT DOCUMENTS

| | | | |
|---|---|---|---|
| EP | 3067037 | A1 | 9/2016 |
| JP | 200481819 | A | 3/2004 |
| JP | 2004283554 | A | 10/2004 |
| JP | 201712798 | A | 1/2017 |
| WO | 2006099441 | A2 | 9/2006 |
| WO | 2012168235 | A1 | 12/2012 |
| WO | 2017009822 | A1 | 1/2017 |

* cited by examiner

CONNECTOR FOR CONNECTING A MEDICAL INJECTION DEVICE TO A CONTAINER AND ASSEMBLY COMPRISING SAID CONNECTOR AND MEDICAL INJECTION DEVICE

CROSS-REFERENCE TO RELATED APPLICATIONS

This application is the United States national phase of International Application No. PCT/EP2020/078024 filed Oct. 7, 2020, and claims priority to European Patent Application No. 19306315.3 filed Oct. 8, 2019, the disclosures of which are hereby incorporated by reference in their entirety.

BACKGROUND OF THE DISCLOSURE

The disclosure relates to a connector for connecting a medical injection device to a container. The disclosure also relates to an assembly comprising said connector and medical device, and to a method for filling the medical injection device with a composition contained in a container by connecting said injection device to the container with the connector.

DESCRIPTION OF RELATED ART

In the field of medicament packaging, it is known to store a drug content, in the form for example of a lyophilized drug, a power drug or an active substance of a drug, in a medical container usually referred to as a "vial". A vial is typically made of glass and is sealed by an elastomer septum that is crimped by an aluminum cap. A portion of elastomer at the center of the septum is covered by plastic part or aluminum part which can be removed by the healthcare professional prior reconstitution procedure so that the healthcare professional can access to a center portion in rubber that can be pierced by a needle of an injection device such as a syringe.

To reconstitute the drug, the user uses usually a disposable plastic syringe to transfer the diluent from an ampoule or a vial into the vial containing the lyophilized drug or power drug. When the diluent is already stored in a prefilled syringe, typically made of glass, the healthcare professional transfers the diluent directly from the syringe to the vial containing the lyophilized drug or power drug. The healthcare professional uses for this transfer a needle to pierce the rubber septum of the vial.

However, this process comprises a significant number of steps.

Moreover, during the whole process, the needle tip may be damaged due to the removal of the needle shield, piercing of the septum of the vial, and/or misalignment during insertion of the needle. A damaged or bent needle may lead to injuries of the patient during the injection of the drug.

Another major drawback of the known processes is that, during the reconstitution process, the needle of the syringe is left free and unprotected. This represents a high risk of accident for the user as well as for the patient or any person around who were to come into contact with the needle, and may lead to needle stick injuries.

Furthermore, when the user withdraws the reconstituted drug from the vial through the needle, the user needs to adjust the length of the portion of the needle that is inserted in the vial as the amount of drug in the vial decreases. In a practical way, the user needs to slowly draw the needle back from the container by pulling the syringe away from the vial, so that the opening of the needle constantly remains in contact with the drug, in other terms, below the surface of the drug.

Not only this handling is hard to perform, but also such movement of the needle in the vial may lead to a loss of a significant amount of drug that remains in the vial.

Document WO2012/168235 describes a connection device that comprises a subassembly including a plug intended to be connected to a medical container, a needle extending from the plug, a sealing sleeve arranged around the needle, and a base with a penetrating member. The base defines an inner volume that is configured to accommodate the subassembly. The penetrating member is configured to pierce the septum of a vial, defines an inner volume adapted to accommodate the needle, and comprises an opening for transferring a composition from the medical container connected to the needle to the vial, for reconstituting a drug contained in the vial.

However, this connection device cannot be connected to a prefilled syringe filled with diluent for a long-term storage, only designed as a disposable device for extemporaneous storage. Indeed, the needle is not sealed when the connection device is connected to the syringe. Thus, the sterility of the content of the syringe cannot be ensured.

Moreover, the penetrating member is exposed, which represents a risk of injury to the user or any person around the device.

Other examples of connection devices are given in WO2006/099441, EP0499481, WO2017/009822, and EP3067037.

SUMMARY OF THE DISCLOSURE

The disclosure aims to provide a connector that overcomes the drawbacks detailed previously. In that matter, the disclosure aims to provide a connector for connecting a prefilled medical injection device, such as a syringe or the like, to a container, such as a vial or the like, that is more intuitive to use and to set up, comprises a reduced number of constitutive parts and reduces the overall number of steps to transfer the reconstitute the drug.

To this end, one object of the disclosure is a connector for connecting a medical injection device having a distal tip, a needle extending from the distal tip and a sleeve extending around the tip, the sleeve comprising an inner threaded portion, to a container comprising a collar closed by a pierceable septum, said connector comprising:

- a proximal part configured to sealingly engage the tip of the injection device so as to enclose at least a part of the needle, the proximal part comprising an outer threaded portion configured to be removably screwed to the inner threaded portion of the sleeve,
- a distal part configured to be connected to the container, comprising a skirt configured to extend around the needle when the connector is connected to the injection device, the skirt being adapted to enclose at least the collar of the container when connected to said container,
- a needle shield configured to be mounted on the needle, so as to sealingly enclose at least the tip of the needle, the needle shield extending through the skirt and comprising a closed distal portion and a proximal portion comprising an opening, the needle shield being configured to be pierced by the needle inserted via the opening for sealingly enclosing said needle.

The threaded portions of the sleeve and the proximal portion ensure a tight, reliable, and sealed connection between the injection device and the connector that prevents any leak of a composition flowing between the injection device and the connector, which is especially important for long term storage pre-filled syringes. Moreover, screwing and unscrewing the connector to the injection device is easy, fast, and does not require physical strength, contrary to, for example, a snap-in connection.

According to other optional features of the device of the disclosure:

- the needle extends within the skirt for at most half of the length of the skirt, preferably at most a third of the length of the skirt. Since only a small portion of the needle is accessible, the risk of damaging or bending the needle when the needle pierces the septum of the container is limited. The risk of injury by pricking the user, the patient, or any person around is also limited due to the skirt completely covering the needle, especially the needle tip;
- the skirt comprises at least one rim that extends radially inwardly, said rim being configured to engage a recess of the collar of the container when the skirt is connected to the container;
- the skirt is adapted to deflect radially outwardly when connected to the container;
- the skirt is provided with a plurality of flexible tabs separated from each other by recesses, the flexible tabs being configured to deflect radially outwardly when the skirt is connected to the container;
- the needle shield protrudes distally from the skirt;
- the skirt comprises a flange, and the proximal part of the needle shield is configured to be sealingly and at least partially inserted into a groove provided in the flange so that said proximal part of the needle shield radially abuts an inner surface of the groove;
- the needle shield further comprises a ring protruding radially outwardly from a body of the needle shield, said ring being configured to abut the skirt when the needle shield is mounted on the needle for retaining said needle shield on the needle;
- the ring is configured to abut the rim of the skirt when the needle shield is mounted on the needle;
- the ring is integral with the needle shield;
- the distal part of the needle shield comprises a grip portion configured to protrude distally away from the skirt when the needle shield is mounted on the needle, and configured to be handled by a user for mounting or removing the needle shield from the needle;
- the grip portion comprises a stem that protrudes from the skirt, and a flange substantially perpendicular to the stem that acts as a handle configured to be gripped between a user's fingers to manipulate the needle shield;
- the proximal part and the distal part of the connector are in a single piece.

Another object of the disclosure is an assembly comprising:

- a medical injection device comprising a barrel, a tip extending distally from the barrel and a sleeve extending around the tip, the sleeve being provided with an inner threaded portion, and
- a connector as described previously,
- wherein the proximal part of the connector is in threaded engagement with the threaded portion of the sleeve and sealingly engages the tip of the medical injection device.

According to a preferred embodiment of the assembly, the barrel, the tip and the sleeve are integrally formed as a single piece.

The disclosure also relates to a method for transferring a composition from a container sealed by a pierceable septum, to a medical injection device, the method comprising the following steps:

- providing a prefilled medical injection device with a tip and a sleeve extending around the tip, the sleeve comprising a threaded portion, and a connector as described previously screwed to the tip via the threaded portion of the sleeve,
- removing the needle shield from the needle so as to expose said needle,
- connecting the connector to the container by engaging the distal part of the connector with the container, the needle thereby perforating the septum of the container,
- transferring into the container a first composition contained in the injection device through the needle,
- mixing the first composition with a second composition contained in the container,
- drawing the mixed compositions from the container back to the injection device, unscrewing the injection device from the connector.

BRIEF DESCRIPTION OF THE DRAWINGS

Further features and advantages of the disclosure will become apparent from the detailed description to follow, with reference to the appended drawings, in which.

DETAILED DESCRIPTION

Figure 1A:
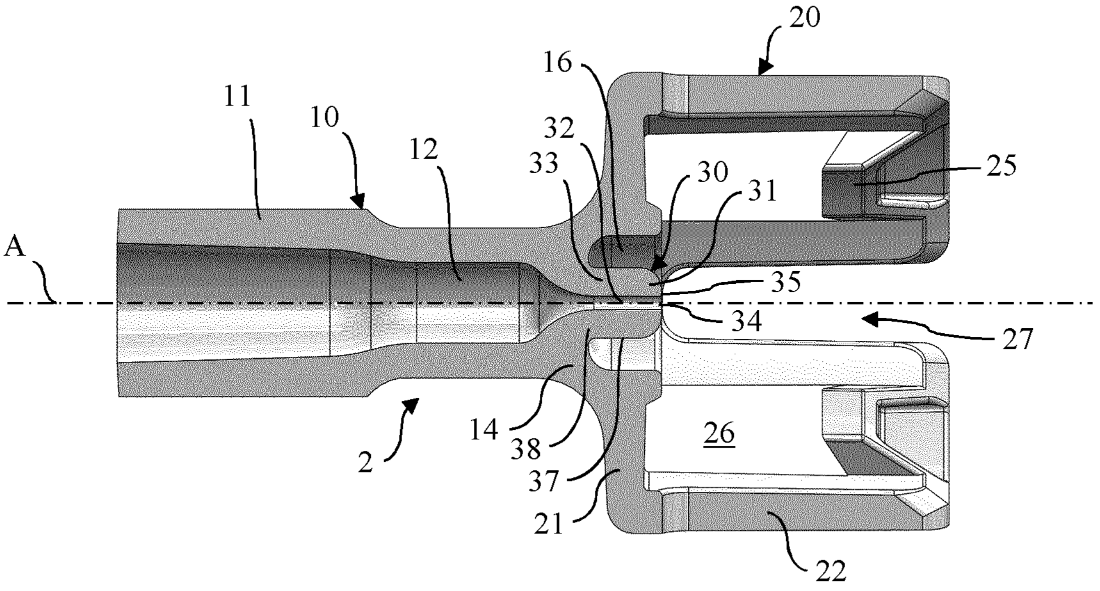
FIG. 1A is a side cross-sectional view of an embodiment of a connector of the disclosure, with no needle shield.
Figure 1B:
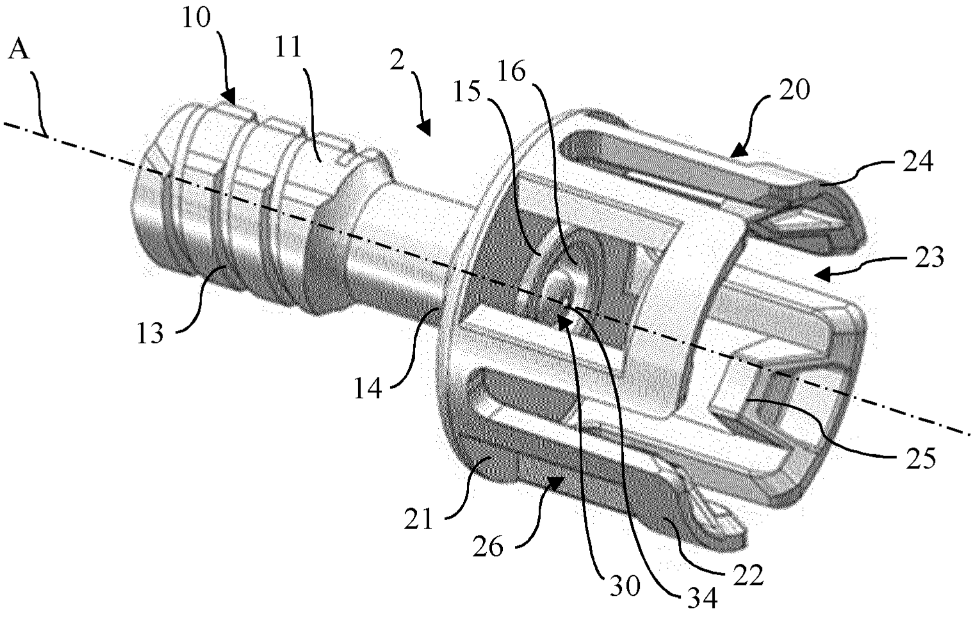
FIG. 1B is a general perspective view of the connector of FIG. 1A.
Figure 2:
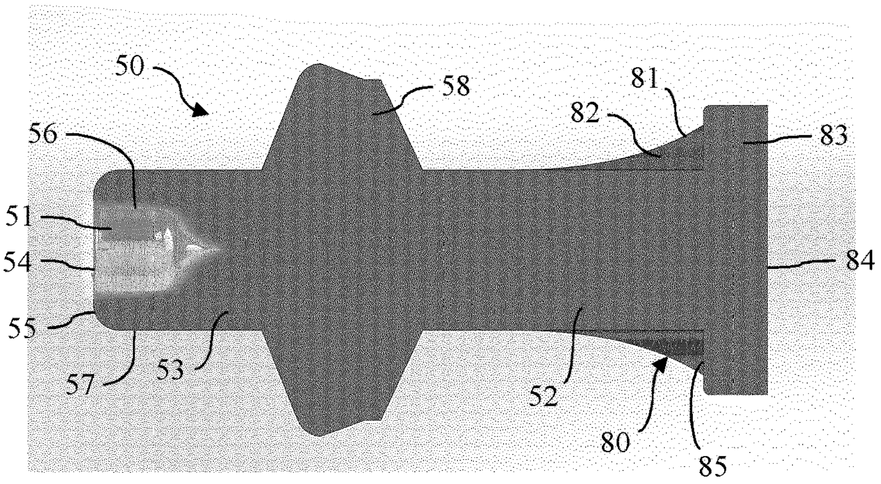
FIG. 2 is a side cross-sectional view of a needle shield configured to be mounted on the needle of the connector for sealingly enclosing at least the tip of the needle.
Figure 3:
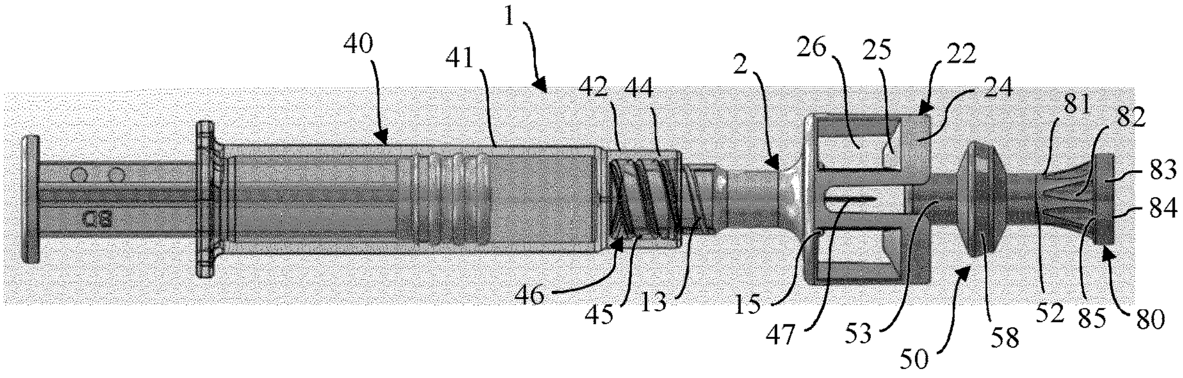
FIG. 3 is side perspective view of an assembly of the disclosure obtained by connecting the connector to a medical injection device, wherein the medical injection device is provided with a tip having a needle attached thereto, and a sleeve extending around the tip, the needle shield being aligned with and at a distance from the needle.
Figure 4:
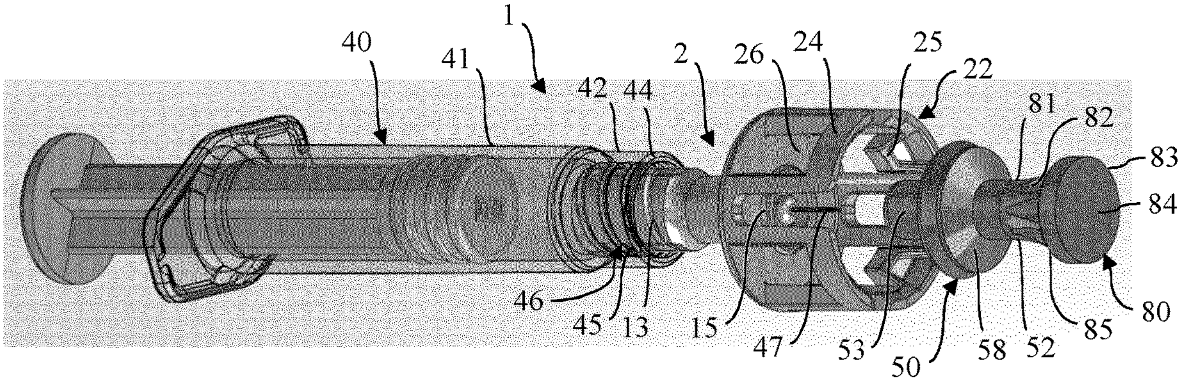
FIG. 4 is perspective view of the assembly of FIG. 3.
Figure 5:
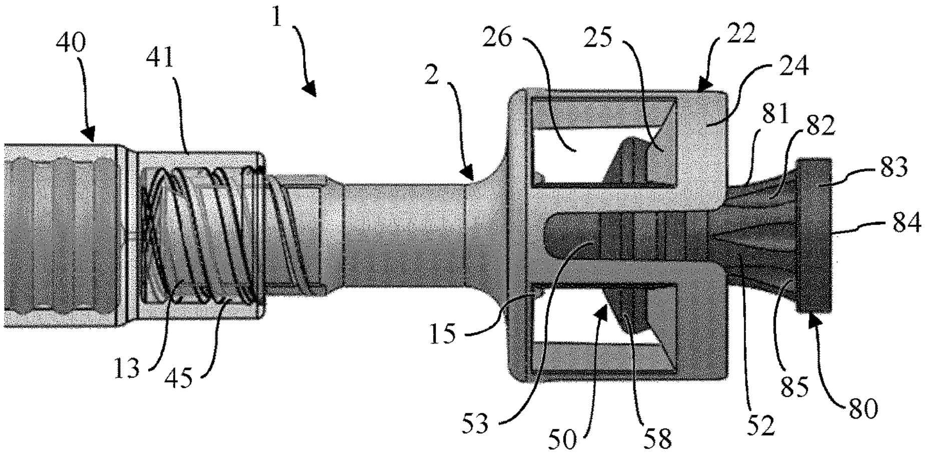
FIG. 5 is a side perspective view of the assembly, wherein the needle shield is mounted on the needle of the medical container.
Figure 6:
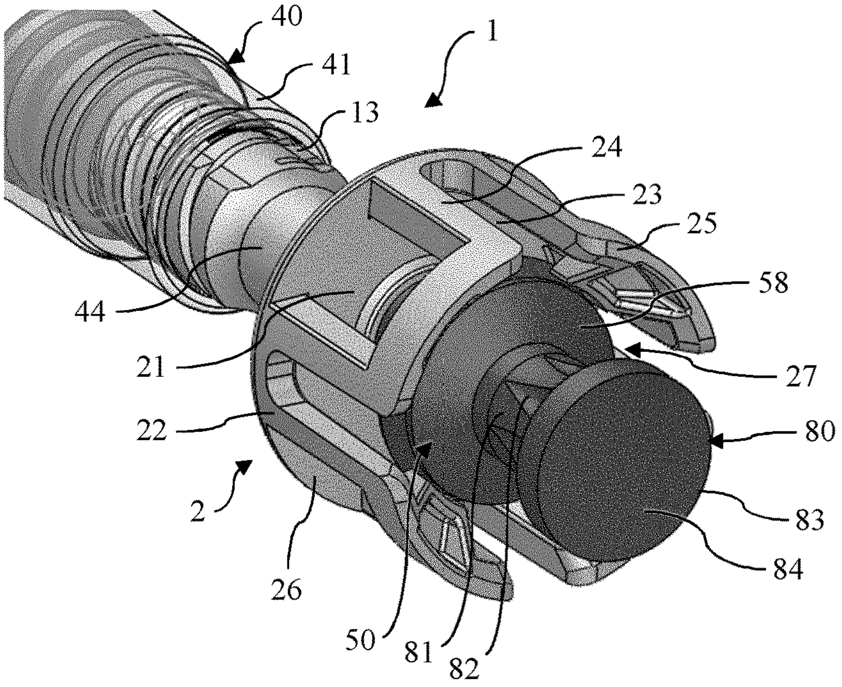
FIG. 6 is a perspective view of the assembly of FIG. 5.

A first object of the disclosure is a connector for connecting a medical injection device to a container closed by a pierceable septum. An embodiment of the connector is represented in FIGS. 1A and 1B.

The connector and the injection device connected to each other form an assembly. An embodiment of such an assembly is represented in FIGS. 3 to 7 in different views.

The connector 2 is connected to the injection device 40 provided with a needle 47. Said needle 47 is configured to pierce the septum 63 of the container when the distal part 20 is connected to the container. The injection device is preferably a pre-filled syringe.

In reference to FIGS. 1A and 1B to 7, the connector 2 extends along a longitudinal axis A. The connector 2 comprises a proximal part 10 configured to be connected to the tip 42 of the injection device 40, a distal part 20 configured to be connected to a container 60, and a needle shield 50 configured to be mounted on the needle 47, so as to sealingly enclose at least the tip of the needle. The container 60 is preferably a vial.

The tip 42 of the injection device extends distally from the barrel 41 and is advantageously of a cylindrical or frustoconical shape.

A sleeve 44 extends around and at a distance from the tip in the radial direction, thereby defining a housing 46 between the tip and the sleeve.

The sleeve 44 comprises an inner surface provided with a threaded portion 45 that faces the outer surface 43 of the tip.

Such a combination of the tip and the sleeve may be known as a Luer lock™ connection, although the disclosure is not limited to a connection sold under this designation.

According to one embodiment, the barrel, tip and sleeve are made as a single part, by plastic injection molding. According to another embodiment, the barrel is made in glass, whereas the tip and sleeve are made in plastic.

The proximal part 10 of the connector comprises a body 11 that encloses a hollow inner volume 12. The outer surface of the body is provided with a threaded portion 13 which is configured to be screwed to the corresponding threaded portion 45 of the inner surface of the sleeve 44. The inner surface of the body has a shape complementary to the outer surface of the tip to ensure a tight connection with the tip.

The connector 2 is connected to the injection device 40 by inserting the body 11 of the connector in the housing 46 between the tip and the sleeve, by screwing the threaded portions 13, 45 of the body 11 and the sleeve 44. At the same time, the tip 42 of the injection device is inserted in the inner volume 12 of the proximal part up to a distal region 14 of the proximal part.

The screwing of the proximal part 10 of the connector to the sleeve 44 of the injection device ensures a tight and sealed connection between the connector 2 and the injection device 40, preventing any movement of the connector and the injection device relative to each other, and preventing any leakage from the assembly 1 to the outside of said assembly.

The distal part 20 of the connector comprises a flange 21 which extends radially outwardly from the distal region 14 of the proximal part 10, and a skirt 22 which extends from the flange in the distal direction.

The skirt 22 is adapted to be connected to the collar 62 of the container. To that end, the skirt has a substantially cylindrical shape that matches the shape of the collar. Hence, when connected to the container, the skirt encloses the collar of the container. The skirt 22 may comprise at least one rim 25 that extends radially inwardly. Such rim 25 is configured to abut against a recess 64 of the collar 62 of the container 60 when the skirt 22 is connected to the container, thereby preventing the connector 2 from being pulled away in a proximal direction from the container 60. In particular, such rim prevents accidental removal of the connector during storage.

According to a preferred embodiment, the skirt 22 comprises a plurality of flexible tabs 24 separated from each other by recesses 23, said tabs being adapted to deflect radially outwardly for connecting the skirt to the container. The skirt thereby further fits to the dimensions of the collar, making the connection of the skirt to the container easier.

The tabs 24 are provided at their distal end with borders 25 that extend radially inwardly. When the skirt 22 is connected to the container 60, the tabs 24 abut against the recess 64 of the collar, thereby preventing the connector 2 from being pulled away in a proximal direction from the container 60. In particular, such borders prevent accidental removal of the connector during storage.

According to a preferred embodiment, the tabs 24 comprise hollow portions 26. The presence of the hollow portions facilitates the demolding of the connector during the manufacture, and further increase the ability of deflection of the tabs. In addition, the weight of the connector is reduced.

According to a preferred embodiment, the connector comprises a nozzle 30, that is particularly visible in FIGS. 1A and 1B.

The nozzle 30 has a cylindrical shape delimited by an outer surface 37 and extends distally in the hollow inner volume 12 of the proximal part 10 of the connector along the axis A, up to the flange 21. The internal volume 32 of the nozzle is in fluidic communication with said inner volume 12 of the proximal part of the connector, and extends up to an opening 34 provided in the distal end 35 of the nozzle. The opening 34 creates a fluidic connection between the medical injection device 40 and the container 60 when connected thereto.

The nozzle 30 is configured to receive a distal portion of the needle, in alignment with the proximal portion of the needle attached to the tip 42 of the injection device 40, along the axis A. In that way, the needle extends within the inner volume of the nozzle 30 through the opening 34 and protrudes from thereon within the skirt 22.

The nozzle is configured to be inserted in the needle shield along with the needle, so that the tip of the needle, including its outlet 49, is sealingly enclosed in the needle shield.

When the connector is connected to the injection device, the needle 47 is completely covered by the skirt 22. Hence, the skirt acts as a rigid cover that reduces the risk of a user pricking himself or any person around when the needle is uncovered. Moreover, the skirt enables to auto-center the needle 47 with respect to the pierceable septum 63 and thus eases the pricking of the pierceable septum 63 by the needle.

Preferably, the needle 47 extends within the skirt 22 for at most half of the length of the skirt 22, preferably at most a third of the length of the skirt 22. In that way, the risk of injury is even lower, and the needle is optimally auto-centered before it pierces the septum 63 of the container.

According to a preferred embodiment, the nozzle 30 comprises a tapered pipe 33 that tapers away from the proximal part of the connector and a straight pipe 31 that extends further distally up to its distal end 35.

The connector 2 is advantageously made in a single piece. In other terms, the proximal part 10, the distal part 20, and the nozzle 30 are formed in a single piece of material, such as a plastic material. An example of appropriate material is polypropylene.

Concerning the needle shield 50, an embodiment is illustrated in FIGS. 2 to 7.

The needle shield 50 comprises body having a closed distal part 52, a proximal part 53 provided with an opening 54, and a cavity 51 that extends in the body from the opening towards the distal part.

The cavity 51 has a shape that matches that of the nozzle 30 so as to allow the insertion of the nozzle in the cavity. As visible in FIG. 2, the cavity 51 has a cylindrical shape that tapers distally so as to match the distal end of the nozzle and to facilitate the insertion of the needle.

The needle shield 50 is positioned on the needle 47 before connecting the connector 2 with the container 60, in particular during storage of the connector. When mounted on the needle, said needle pierces the body of the needle shield and at least the tip of the needle is thus sealingly enclosed in said needle shield. The needle shield thereby prevents any injury to a person at the vicinity of the assembly. To the same purposes, the needle shield is preferably made in a flexible material, such as elastomeric material, for example rubber or thermoplastic elastomer. This kind of material also allows the body of the needle shield to be pierced by the needle.

Moreover, the needle shield 50 prevents any contamination of the needle from the external environment during storage.

The nozzle 30 is inserted in the cavity 51. In that way, the needle shield is better secured in position on the needle.

Figure 7:
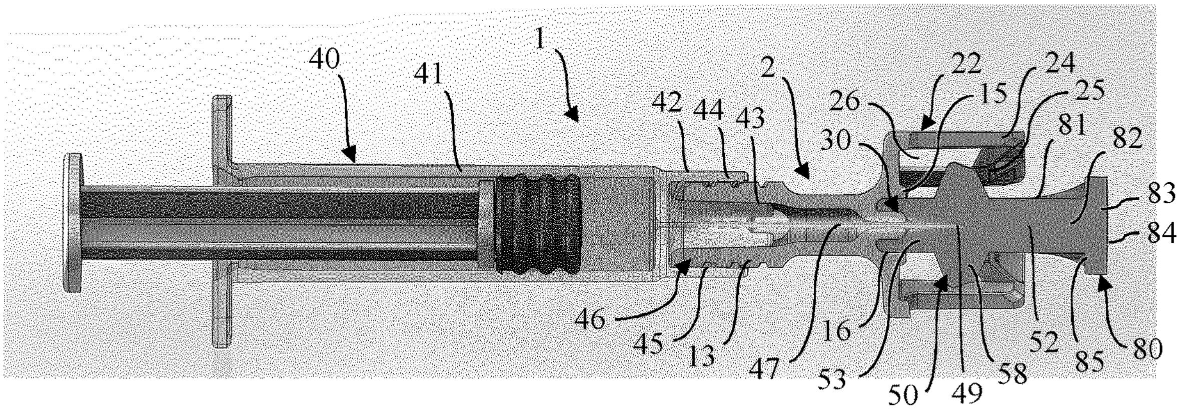
FIG. 7 is a side sectional view of the assembly of FIG. 5.

As particularly visible in FIG. 7, the proximal part 53 of the needle shield is preferably configured to be sealingly inserted into the flange 21 of the connector 2. In particular, the proximal end 55 of the needle shield is inserted into a groove 16 provided in the flange 21 around the base 38 of the nozzle 30. In that way, the proximal end 55 of the needle shield is griped in the groove 16 and radially abuts the flange 21.

To provide a greater abutment surface, the flange 21 may comprise a rim 15 that extends distally therefrom, around the base 38 of the nozzle. This abutment maintains the proximal part 53 of the needle shield onto the nozzle 30, as well as ensuring an optimal sealing of the nozzle and the needle. This abutment is particularly useful when the needle shield is made in a flexible material, wherein the proximal end 55 of the needle shield is prone to extend radially outwardly due to the nature of the material.

As such, optimal sealing of the nozzle 30 is achieved by the contact between:

- the inner surface 56 of the needle shield and the outer surface 37 of the nozzle, along the nozzle 30, from its base 38 to its distal end 35, and/or
- the outer surface 57 of the needle shield and the inner surface of the groove 16 or the rim 15, at the base 38 of the nozzle.

Preferably, the needle shield 30 further comprises a ring 58 that protrudes radially from and around the needle shield. The ring 58 is preferably integral with the needle shield. The ring 58 and the needle shield are preferably made in the same material. The ring 58 is configured to abut the rim 25 of the skirt 22 when the needle shield 50 is mounted on the needle 47. This abutment prevents the needle shield from being pulled off during sterilization, handling, and/or transportation of the connector.

Advantageously, the distal part 52 of the needle shield 50 comprises a grip portion 80 configured to protrude distally away from the skirt when the needle shield 50 is mounted on the needle 47. The grip portion 80 is preferably integral with the needle shield. The grip portion 80 and the needle shield are preferably made in the same material. The grip portion 80 is configured to be handled by a user for mounting or removing the needle shield 50 from the needle.

The grip portion 80 preferably comprises a stem 81 that extends in the distal direction, parallel to the longitudinal axis A, from the rest of the needle shield. The stem 81 extends distally from the ring and protrudes sufficiently from the skirt to be gripped by the user without the fingers of the user contacting the skirt 22, thereby preventing contamination of the skirt by the user.

The outer surface 82 of the stem may be advantageously be provided with grip marks that improve the grip of the fingers of the user onto said surface 82, thereby facilitating the positioning and the removal of the needle shield. The grip portion 80 further comprises a flange 83 that is substantially perpendicular to the stem 81. The flange 83 acts as a handle the user may grip to manipulate the needle shield easily. In particular, when handling the needle shield 50, the thumb of the user may abut the distal surface 84 of the flange 83 and the index and middle finger of the user may abut the proximal surface 85 of the flange, which facilitates the removal of the needle shield by helping him overcoming the resistance caused by the abutment of the ring 58 against the rim 25 of the skirt 22.

Figure 12:
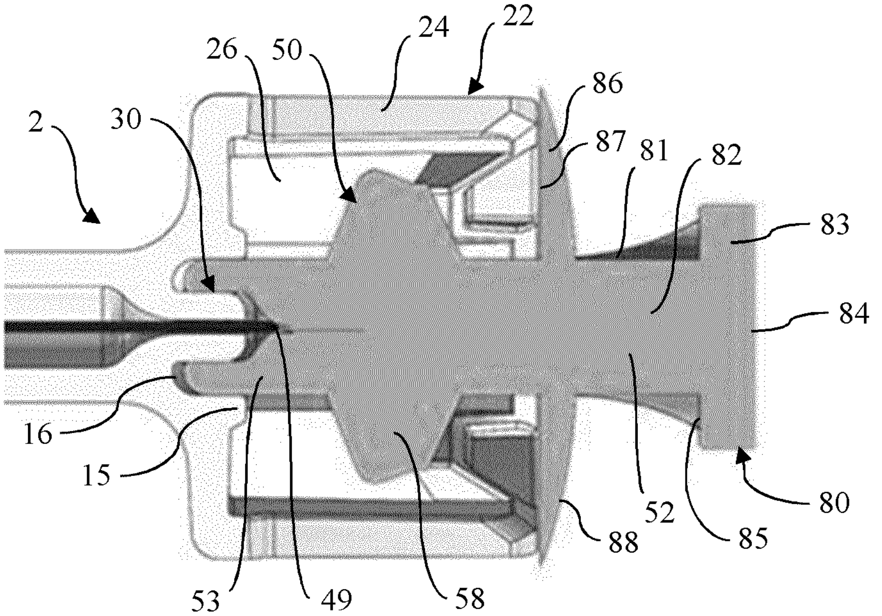
FIG. 12 is a side section view of an assembly of the disclosure.

According to a preferred embodiment illustrated in FIG. 12, the needle shield 50 may be provided with an umbrella 86, preferably substantially circular, which extends radially outwardly from the stem 81 of the grip portion 80. The umbrella 86 comprises a proximal face 87 that faces the skirt 22, and a distal face 88 opposite the proximal face.

The umbrella 86 is preferably configured to abut the skirt 22 when the needle shield is pushed in the proximal direction toward the skirt. To that end, the diameter of the umbrella 86 is advantageously substantially equal to or greater than the diameter of the skirt 22 so as to cover said skirt when the connector is observed from the distal face 88 of the umbrella 86.

When removing the needle shield 50 from the needle 47, the umbrella prevents the fingers of the user from contacting the skirt 22, thereby preventing contamination of said skirt by the user.

A method for transferring a composition from the container sealed by a pierceable septum to the medical injection device will now be described in the following, in reference to the FIGS. 7 to 11.

Optionally, the connector and the injection device are connected to form the assembly to be stored before use.

The connector 2 is connected to the injection device 40, by screwing the proximal part of the connector to the tip 42 of the injection device. To this end, the body 11 of the proximal part is inserted in the housing 46 and rotated to ensure screwing of the respective threaded portions 13, 45 of the connector and the injection device. The tip 42 of the injection device is inserted in the inner volume of the proximal part and the needle 47, when present, extends through the nozzle 30. The needle shield 50 is then mounted on the needle 47 so as to sealingly enclose said needle. The assembly 1 obtained is represented in FIG. 7.

In order to use the assembly, the needle shield 50 is removed from the needle 47.

A distal portion of the needle is uncovered and extends within the skirt 22 from the nozzle 30.

Figure 8:
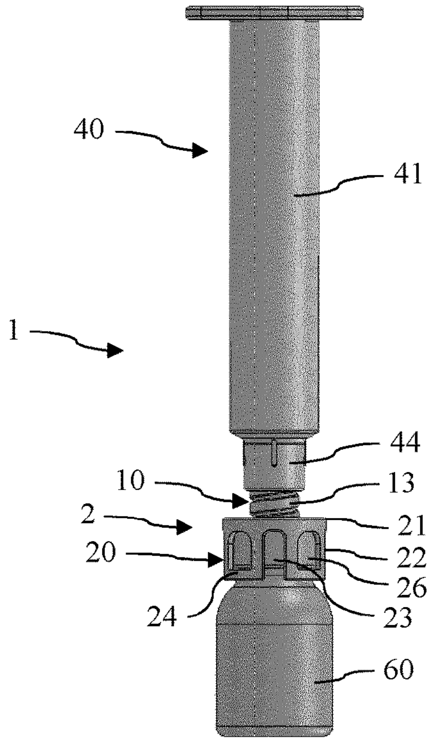
FIG. 8 is a side view of the assembly after the needle shield has been removed, wherein the injection device is connected to a container via the connector, so as to transfer a first composition contained in the injection device.

In reference to FIG. 8, the connector 2 is then connected to the container 60. The distal part 20 of the connector engages the container 60, and the distal tip of the needle perforates the septum 63 of the container.

In this configuration, the skirt 22 of the connector is firmly attached to the collar 62 of the container and encloses said collar.

Figure 9:
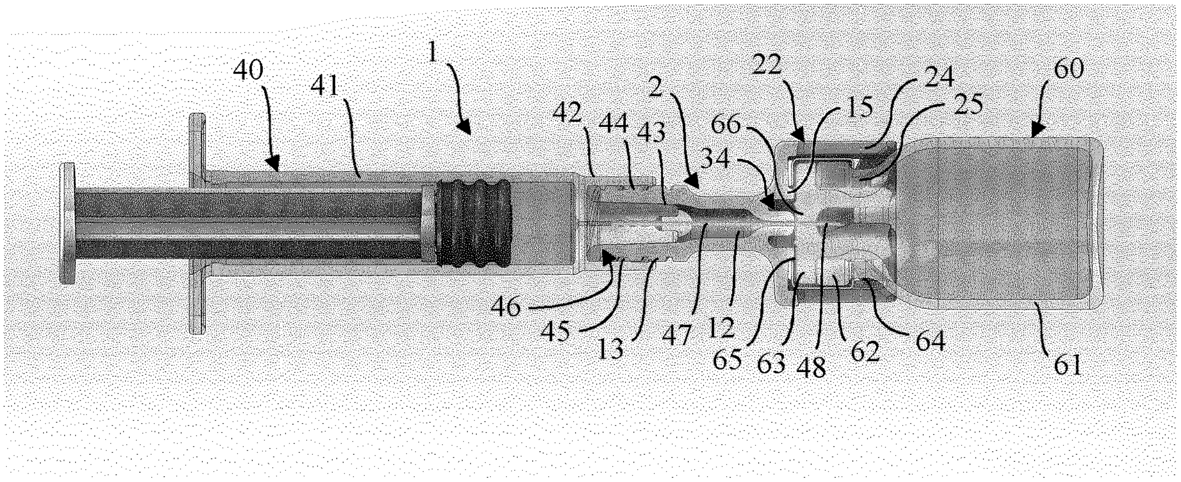
FIG. 9 is a side sectional view of the assembly connected to a medical container.

As represented in FIG. 9, a portion of the needle, including its outlet 49, penetrates inside the container 60. The flange 21 of the distal part 20 abuts the collar 62 of the container, so that the needle 47 cannot go further distally inside the container. Hence, a portion 48 of the needle is located inside the container. The length of this portion 48 of the needle depends on the length of the needle itself and the structure of the connector, and may be adjusted when the connector is being designed.

The skirt 22 contacts the container, and the tabs 24 cover the collar 62. The tabs 24 may advantageously deflect radially outwardly to facilitate the connection. The borders 25 of the tabs abut against the recess 64 of the collar, thereby preventing the connector 2 from being separated from the container. The container 60 is thus maintained in a fixed position to the connector 2.

Since the needle 47 extends along the axis A in the inner space 27 of the skirt and said skirt encloses the collar of the container, the needle 47 is centered relative to the top surface 65 of the septum 63 of the container. This allows the insertion of the needle at the center of said top surface 65 of the septum, said needle piercing the center portion 66 of the septum typically made of elastomer that is not covered by aluminum. Since the insertion force is quite low due to the small diameter of the needle, and only a small portion of the needle extends within the skirt of the connector, the deformation of the needle 47 is negligible.

Since the skirt 22 extends more distally than the needle 47, the skirt 22 begins engaging the collar 62 of the container as the needle is proximally remote from the septum. Hence, thanks to the skirt, the needle is centered relative to the top surface 65 of the septum 63 and guided to the center portion 66 of the septum until full engagement of the connector onto the container.

A first composition, contained in the injection device, is then transferred into the container prefilled with a second composition. To that end, the user pushes the plunger rod (not represented) of the injection device in the distal direction.

The composition flows along the needle 47, through the nozzle, and is expelled from the needle via the outlet 49 and transferred into the container 60.

The first composition is then mixed with the second composition. To that end, the user may handle both the assembly 1 and the container 60, and shake them gently so as to allow the mixing.

The mixed compositions are then drawn back to the injection device.

To that end, the assembly 1 and the container 60 are turned upside down, and the user pulls the plunger rod of the injection device, thereby creating a suction effect through the needle. In this position, the outlet 49 of the needle remains immersed in the mixed compositions regardless the amount of compositions remaining in the container. Therefore, complete withdrawal can be achieved with no need to adjust the length of the portion 48 of the needle inserted in the container. In other terms, the user does not need to move the needle relative to the container as in the prior art for keeping the needle immersed in the mixed compositions as long as the withdrawal goes. This saves the user from having to perform complicated and imprecise manipulations in order to adjust the length of the portion of needle inserted in the container, and makes the transfer between the injection device and the container much faster and easier.

The mixed compositions flow from the container 60 into the needle 47 via the outlet 49 of the needle, and is then transferred into the barrel 61 of the injection device.

During withdrawal, the connection between the proximal part of the connector and the tip and sleeve of the injection device ensures the sealing of the assembly and prevents any leak from the assembly to the outside of said assembly.

Figure 10:
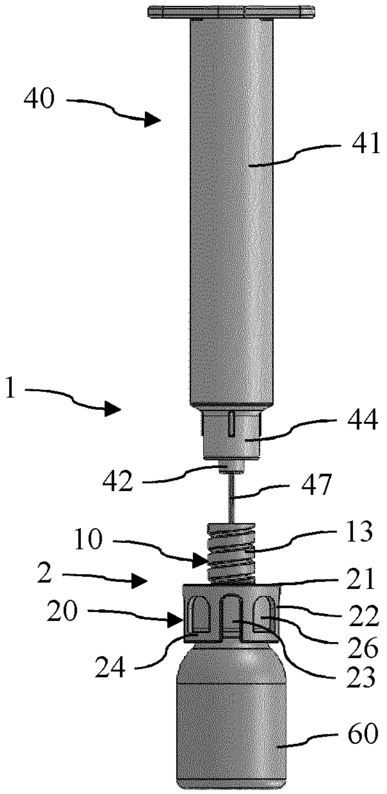
FIG. 10 is a side view of the injection device and connector, wherein the injection device is being removed from the connector after withdrawal of the composition, the connector remaining connected to the container.
Figure 11:
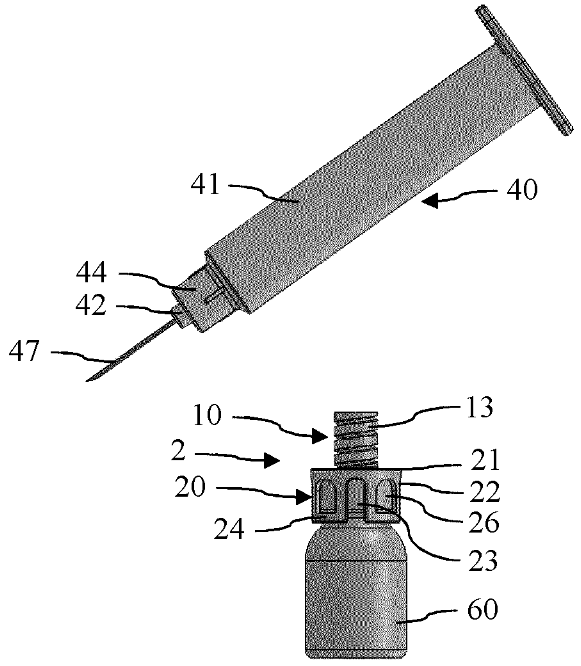
FIG. 11 is a side view of the injection device and connector, wherein the injection device is completely removed from the connector.

In reference to FIGS. 10 and 11, the injection device 40 is then separated from the connector 2. To this end, the body 11 of the proximal part is rotated to cause unscrewing of the respective threaded portions 13, 45 of the connector and the injection device. The tip 42 of the injection device disengages the inner volume of the proximal part, and the needle 47 is removed from the nozzle 30. The connector 2 remains connected to the container 60 and may be further disposed of.

The injection device containing the mixed compositions is then ready to be used.

According to a preferred embodiment, the method described above is related to the reconstitution of a drug, wherein the first composition is a diluent and the second composition is a drug content, such as for example a lyophilized drug or an active substance of a drug.

The invention claimed is:

1. A connector for connecting a medical injection device, the connector comprising:

a proximal part configured to sealingly engage a distal tip of an injection device so as to enclose at least a part of a needle extending from the distal tip, the proximal part comprising an outer threaded portion configured to be removably screwed to an inner threaded portion of a sleeve extending around the distal tip of the injection device, a distal part configured to be connected to a container of the injection device comprising a collar closed by a pierceable septum, the distal part comprising a skirt configured to extend around the needle when the connector is connected to the injection device, the skirt comprises a rim that extends radially inwardly, the rim being configured to engage a recess of the collar of the container when the skirt is connected to the container, and the skirt being configured to enclose at least the collar of the container when connected to the container, and a needle shield configured to be mounted on the needle so as to sealingly enclose at least the tip of the needle, the needle shield extending through the skirt and comprising a closed distal portion and a proximal portion comprising an opening, the needle shield being configured to be pierced by the needle inserted via the opening for sealingly enclosing the needle;

the needle shield comprising a ring protruding radially outwardly from a body of the needle shield, the ring configured to abut the rim of the skirt when the needle shield is mounted on the needle for retaining the needle shield on the needle.

2. The connector according to claim 1, wherein the skirt of the distal part is sized such that, when the connector is connected to the injection device, the needle extends within the skirt for at most half of the length of the skirt.

3. The connector according to claim 1, wherein the skirt comprises at least one rim that extends radially inwardly, the rim being configured to engage a recess of the collar of the container when the skirt is connected to the container.

4. The connector according to claim 1, wherein the skirt is configured to deflect radially outwardly when connected to the container.

5. The connector according to claim 1, wherein the skirt is provided with a plurality of flexible tabs separated from each other by recesses, the flexible tabs being configured to deflect radially outwardly when the skirt is connected to the container.

6. The connector according to claim 1, wherein the needle shield protrudes distally from the skirt.

7. The connector according to claim 1, wherein the skirt comprises a flange, and the proximal portion of the needle shield is configured to be sealingly and at least partially inserted into a groove provided in the flange so that the proximal portion of the needle shield radially abuts an inner surface of the groove.

8. The connector according to claim 1 wherein the ring is integral with the needle shield.

9. The connector according to claim 1, wherein the distal portion of the needle shield comprises a grip portion configured to protrude distally away from the skirt when the needle shield is mounted on the needle and configured to be handled by a user for mounting or removing the needle shield from the needle.

10. The connector according to claim 9, wherein the grip portion comprises a stem that protrudes from the skirt, and a flange substantially perpendicular to the stem that acts as a handle configured to be gripped between a user's fingers to manipulate the needle shield.

11. The connector according to claim 1, wherein the proximal part and the distal part of the connector are in a single piece.

12. An assembly comprising:

a medical injection device comprising a barrel, a tip extending distally from the barrel and a sleeve extending around the tip, the sleeve being provided with an inner threaded portion, and the connector according to claim 1, wherein the proximal part of the connector is in threaded engagement with the threaded portion of the sleeve and sealingly engages the tip of the medical injection device.

13. The assembly according to claim 12, wherein the barrel, the tip and the sleeve are integrally formed as a single piece.

14. A method for transferring a composition from a container sealed by a pierceable septum to a medical injection device, the method comprising:

providing a prefilled medical injection device with a tip and a sleeve extending around the tip, the sleeve comprising a threaded portion, and the connector according to claim 1 screwed to the tip via the threaded portion of the sleeve, removing the needle shield from the needle so as to expose the needle, connecting the connector to the container by engaging the distal part of the connector with the container, the needle thereby perforating the pierceable septum of the container, transferring into the container a first composition contained in the injection device through the needle, mixing the first composition with a second composition contained in the container, drawing the mixed compositions from the container back to the injection device, and unscrewing the injection device from the connector.

* * * * *